United States Patent [19]

Kanda

[11] Patent Number: 5,030,000
[45] Date of Patent: Jul. 9, 1991

[54] FIBER OPTIC PROBE FOR MEASURING REFLECTANCE SPECTRUM

[75] Inventor: Masahiko Kanda, Osaka, Japan

[73] Assignee: Sumitomo Electric Industries, Ltd., Osaka, Japan

[21] Appl. No.: 405,732

[22] Filed: Sep. 8, 1989

[30] Foreign Application Priority Data

Sep. 9, 1988 [JP] Japan .................... 63-119058[U]

[51] Int. Cl.$^5$ .................................... G01N 33/48
[52] U.S. Cl. .................................... 356/40; 350/96.1; 356/73.1
[58] Field of Search .................... 356/39–42, 356/336, 300, 319, 324, 73.1; 350/96.1, 96.25, 96.24; 427/9; 250/554

[56] References Cited

U.S. PATENT DOCUMENTS

| | | | |
|---|---|---|---|
| 4,295,470 | 10/1981 | Shaw et al. | 356/41 |
| 4,338,352 | 7/1982 | Bear et al. | 427/9 |
| 4,395,120 | 7/1983 | Takahashi | 356/125 |
| 4,573,761 | 3/1986 | McLachlan et al. | 350/96.1 |
| 4,615,583 | 10/1986 | Tsuno et al. | 350/96.26 |
| 4,623,788 | 11/1986 | Kern et al. | 250/554 |

FOREIGN PATENT DOCUMENTS

| | | |
|---|---|---|
| 0063431 | 10/1982 | European Pat. Off. . |
| 0093927 | 11/1983 | European Pat. Off. . |
| 0216138 | 4/1987 | European Pat. Off. . |
| 22061098 | 6/1971 | Fed. Rep. of Germany . |
| 2596530 | 10/1987 | France . |
| 59-113749 | 8/1984 | Japan . |

Primary Examiner—Richard A. Rosenberger
Assistant Examiner—Hoa Pham
Attorney, Agent, or Firm—W. G. Fasse; D. H. Kane, Jr.

[57] ABSTRACT

In a fiber optical probe for measuring or sensing a reflectance spectrum, an illuminating light supplying optical fiber (1) and a light receiving optical fiber (2) are coupled in parallel to form a fiber bundle (3). A lens (4) is provided on sensing end surfaces of both types of fibers of the fiber bundle. The fiber bundle is inserted in a heat shrinkable polyethylene tube and the tube is shrunken by heat to form a coating jacket (6). The coating jacket extends beyond the end of the fiber bundle to cover the periphery of the lens, so that the lens is fixed to the fiber bundle.

3 Claims, 3 Drawing Sheets

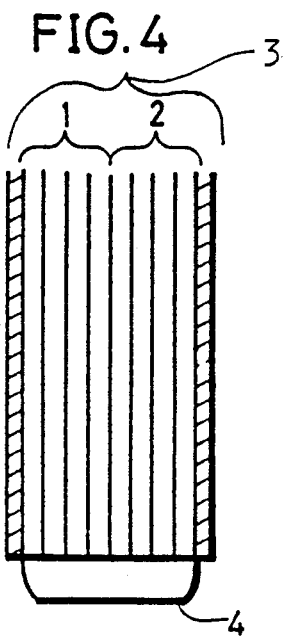
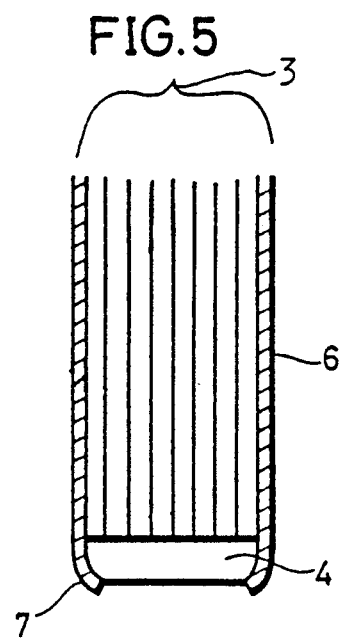
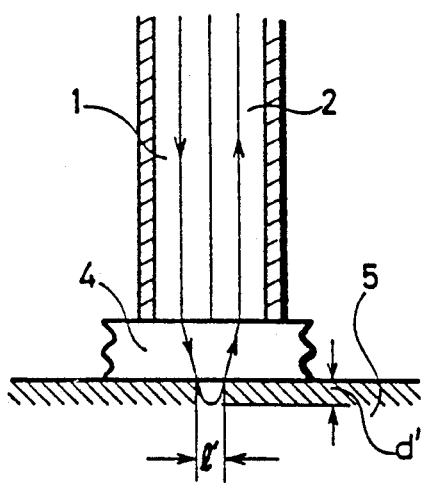

FIBER OPTIC PROBE FOR MEASURING REFLECTANCE SPECTRUM

FIELD OF THE INVENTION

The present invention relates to a fiber optic probe for measuring a reflectance spectrum. More specifically, the present invention relates to a reflected spectrum measuring probe for measuring hemodynamics and oxygen sufficiency such as a volume of hemoglobin and an oxygen saturation in the blood near the surface of a living body for providing information for diagnosing the state of organs such as liver by irradiating the surface of a living body with light and by analyzing the light transmitted through and reflected from the organism in accordance with spectrophotometry.

BACKGROUND INFORMATION

A fiber optic probe for measuring the reflectance spectrum has been used for analyzing the state of pigments in the surface layer of a living body by measuring the light irradiating and reflected from the surface of the organism. Such fiber optic probe comprises a fiber bundle including light illuminating optical fibers and light receiving optical fibers in which a plurality of optical fibers formed of transparent materials such as plastic or glass are bundled in parallel. The fiber bundle is enclosed by a cover on the outer periphery of the bundle. Such a fiber bundle used as a measuring probe is known from, for example, Japanese Utility Model Laying Open No. 59-113749.

The optical fiber generally comprises a core and a jacket covering the core, with the diameter of the core being several 10 μm and the diameter of the jacket or cladding being about 150 μm.

The above mentioned Japanese Utility Model Laying Open No. 59-113749 discloses a metal sleeve holder provided at the outermost periphery so as to protect the probe, and to facilitate the use of the probe. However, what is disclosed in that reference is a number of common bundled optical fibers fiber each consisting of a core and a cladding. The diameter of cladding is about 100 μm and the diameter of the core is about several 10 μm, in a generally used plastic fiber or a glass fiber.

FIG. 1 is an enlarged view of a portion of a conventional probe. FIG. 2 shows a reflectance spectrum with distortions measured by the conventional probe of FIG. 1. FIG. 3 is a graph showing the relationship between the blood volume and the optical density in a sample area.

The conventional probe shown in FIG. 1 includes an illuminating light supplying optical fiber 1 and a light receiving optical fiber 2 arranged next to each other. The light supporting illuminating optical fiber 1 comprises a core 1a and a jacket or cladding 1b, while the light receiving optical fiber 2 comprises as a core 2a and a jacket or cladding 2b. Each of the cores 1a and 2a has a diameter of about several 10 μm and each of the jackets 1b and 2b has a diameter of about 100 μm. Therefore, the distance l between the centers of the illuminating light supply optical fiber 1 and the light receiving optical fiber 2 is about 100 μm.

Now, when a portion of a tissue such as a liver containing much blood, is to be measured by the conventional probe, the reflectance spectrum measured should be as shown by the dotted line in FIG. 2. However, actually the measured result is as shown by the solid line. The reason for this is as follows. As shown by (1) in FIG. 3, the optical density linearly increases as the blood volume increases. When the wavelength of the illuminating light becomes shorter, the effect of scattering increases, so that the increase of the optical density becomes non-linear and is distorted as shown at (2) in FIG. 3. Such a measuring organ probe is not suitable for measuring functions, for example, of the liver containing much blood.

SUMMARY OF THE INVENTION

Therefore, it is an object of the present invention to provide a reflectance spectrum measuring probe capable of measuring a condition of the blood and the like with the distortion in the optical density reduced as much as possible.

Briefly stated, in the present invention, an illuminating light supply fiber for transmitting light and a light receiving fiber for receiving the light transmitted through an organism to be tested, are arranged in parallel to form a fiber bundle, and a lens, is provided over the tip end surfaces of the light supply fiber and the light receiving fiber.

Therefore, in accordance with the present invention, the depth of incident light transmitted through the living tissue, and reflected can be made shallower, so that the measurement can be carried out with little influence of the blood volume whereby organs such as a liver containing much blood, can be tested without distortion. In addition, by providing a number of lenses having different focal length to be attached and detached, various tissue portions or blood in different organs having different blood volumes can be directly measured.

In a preferred embodiment of the present invention, the fiber bundle is covered with a coating layer made of a heat shrinkable tube and the periphery of the lens is covered by an end portion of the coating layer.

Consequently, according to the preferred embodiment of the present invention, the fiber bundle and the lens can be made as an integral component.

In another aspect of the present invention, a plurality of illuminating light supply optical fiber cores and a plurality of light receiving optical fiber cores are arranged next to each other to form a matrix in a jacket, thereby providing an image fiber device. Therefore, in accordance with the present invention the distance, between the centers of the illuminating light supply fiber core and of the light receiving fiber core can be made smaller and therefore the distortion in the reflected spectrum caused by the scattering effect can be avoided, whereby organs holding much blood, as the liver, can be tested by spectrophotometry with a high reliability.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIGS. 4 and 5 are vertical sectional views of one embodiment of the present invention;

FIG. 6 is a vertical sectional view showing one embodiment of the present invention during use;

DETAILED DESCRIPTION OF PREFERRED EXAMPLE EMBODIMENTS AND OF THE BEST MODE OF THE INVENTION

Figure 3:
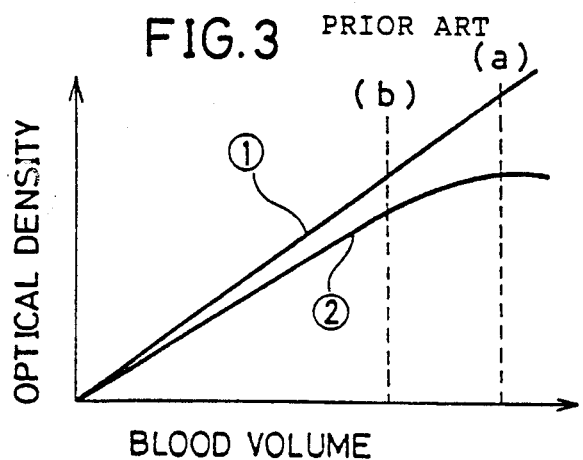
FIG. 3 shows the relationship between the blood volume and the optical density in a sample area.

It has been found that the optical density, which should increase linearly as shown by the line (1) in FIG. 3, as the volume of blood increases, does not increase linearly due to a scattering effect when the wavelength becomes shorter, as shown at (2) in FIG. 3, and that this non-linearity is the cause of distortions in the reflectance spectrum. The invention aims at avoiding the effects of these distortions. More specifically, the blood volume shown in FIG. 3 is the blood volume in the sample area of the measuring probe. Namely, when the sample area is moved from the side (a) to (b) of FIG. 3, the relationship between the volume of blood and the optical density corresponding to that area, becomes linear, enabling a measurement without distortion. The depth d of the sample area shown in FIG. 1 depends on the distance l in FIG. 1, so that the depth d becomes shallower when the distance d is made smaller.

Figure 1:
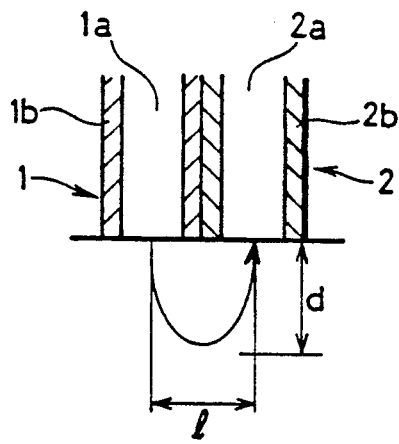
FIG. 1 is vertical sectional view showing a portion of a conventional probe on an enlarged scale.
Figure 2:
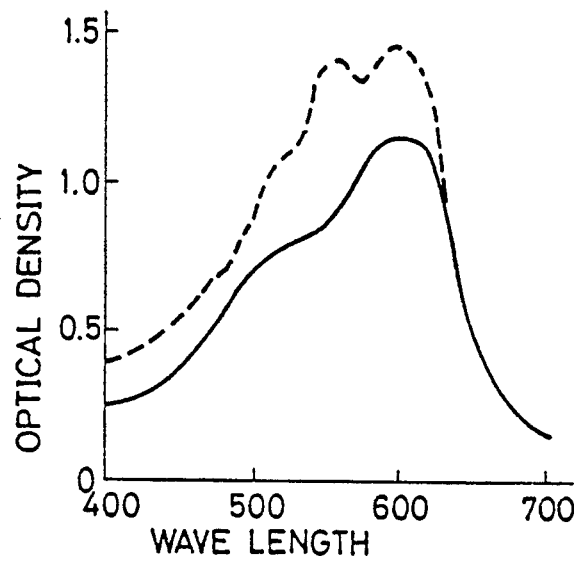
FIG. 2 shows a reflected spectrum with the distortion, measured by the conventional probe of FIG. 1.

The blood volume that influences to the distortion, is the blood volume in the sample area of the probe being measured or tested. The sample area in turn depends on the distance l between the light transmitting optical fiber 1 and the light receiving optical fiber 2, as is apparent from FIG. 1 showing the state of use of the conventional measuring probe. Therefore, when the distance is made smaller such that the sample area is moved from (a) to (b) in FIG. 3 showing the volume of blood, a measurement without distortion becomes possible. More specifically, in the present embodiment, the distance l' shown in FIG. 6 is smaller than l shown in FIG. 1 and therefore the depth d' in FIG. 6 is shallower than d in FIG. 1, whereby the distortion caused by the large blood volume can be made smaller.

One embodiment of the present invention will now be described based on this understanding.

FIGS. 4 and 5 are vertical sectional views of one embodiment of the present invention. Referring to FIG. 4, an illuminating light supplying optical fiber 1 and a light receiving optical fiber 2 are put together in parallel to form a fiber bundle 3 and condenser means 4 formed of, for example, a convex lens is, provided on the end surfaces of the illuminating light supply optical fiber 1 and the light receiving optical fiber 2 at the end portion of the fiber bundle 3. Each of the optical fibers 1 and 2 comprises a bundle of a plurality of fibers formed of a transparent material such as plastic or glass. As shown in FIG. 5, the fiber bundle 3 is inserted into a heat shrinkable polyethylene tube so as to fix the bundle of optical fibers 1 and 2 in a common jacket 6. The tube is shrunk by heat to form the coating jacket 6 having the thickness of 0.3 mm. The jacket coating 6 extends beyond the end of the fiber bundle 3 so that a jacket run 7 covers the periphery of the lens 4. The end portion of the coating jacket 6 forming the rim 7 is bent inwardly by the heat shrinking, so as to hold the lens 4 in its position and to prevent losing the lens 4.

The lens 4 is exchangeable, enabling an adjustment of the degree of condensing the light corresponding to different organs containing different amounts of blood. When the lens 4 is to be exchanged, the diameter of the jacket rim 7 is dilated by a suitable tool sufficiently for removing the lens and replacing it by another lens held in place by the thermoplastic nature or rubber nature of the jacket 6. The coating jacket 6 is made of a polyolefin resin such as polyethylene or rubber tube, and the fiber bundle 3 may be jacketed by inserting the same into the heat shrinkable tube.

FIG. 6 is a vertical sectional view showing one embodiment of the present invention during use. Referring to FIG. 6, the light emitted from the tip end surface of the light transmitting optical fiber 1 is condensed by the lens 4 and enter the living tissue 5 as shown by the arrow in FIG. 6. The incident light is scattered and reflected to enter the light receiving optical fiber 2 again through the lens 4. On this occasion, the distance between the light transmitting optical fiber 1 and the light receiving optical fiber 2 is l' in FIG. 6 and the depth of the light penetration into the living tissue is d'. The depth d' is shallower than in the case of conventional measuring probe, so that the measuring probe of the present invention is capable of measuring organs containing much blood.

The lens 4 employed in this embodiment should preferably be planar, as shown in FIG. 6 in order to enable a close contact between the living tissue 5 and the surface of the lens 4 and to prevent a fluctuation of the measured values caused by a vibration of the probe. In addition, in order to realize a uniform contact and to reduce optical losses, the contact surface of the lens 4 with the illuminating light supplying fiber 1 and the light receiving fiber 2 should be planar. An example of such lens is a selfoc lens.

Figure 7:
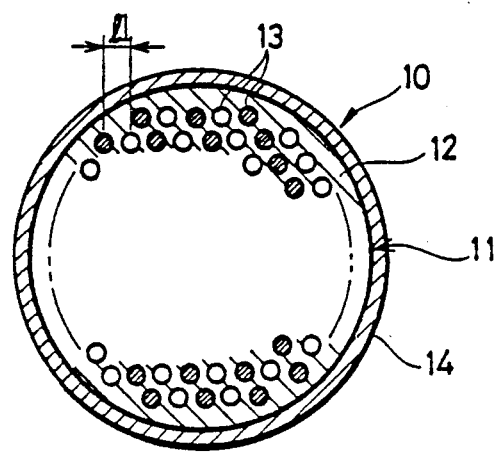
FIG. 7 is a cross sectional view showing an end portion of the probe in accordance with another embodiment of the present invention.
Figure 8:
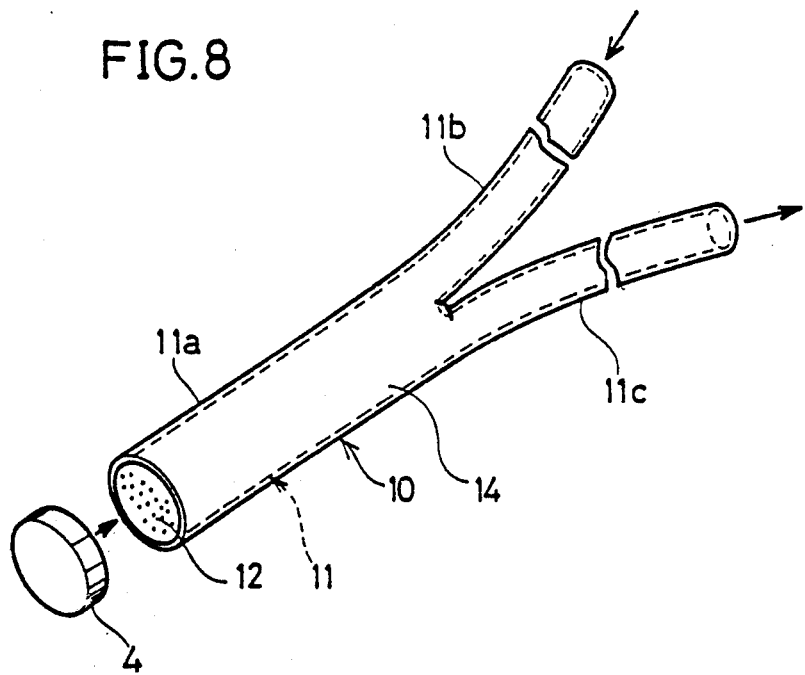
FIG. 8 is a perspective view showing the whole structure of another embodiment of the present invention.

FIG. 7 is a cross section showing an end portion of the probe in accordance with another embodiment of the present invention. FIG. 8 is a perspective view showing the whole structure. The embodiment shown in FIG. 7 reduces the distance l in FIG. 3 to further reduce the depth d without providing a light condensing means.

Referring to FIG. 7, the measuring probe 10 comprises an image fiber 11. The image fiber 11 comprises a number of cores 13 each having a diameter of several 10 $\mu$m arranged in parallel to each other to form a matrix. Each core 13 has a jacket 12 having a jacket thickness of several $\mu$m. At the tip end portion 11a of the probe shown in FIG. 8, one of the cores is used for transmitting illuminating light and the other one is used for receiving light. In FIG. 7, cores for illuminating light are shown white and the cores for receiving light are hatched so as to facilitate understanding.

These cores 13 are divided into groups, two one group is formed by the light transmitting cores and the other group is formed by the light receiving cores. The two groups are branched at an intermediate portion of the measuring probe 10 as shown at 11b and 11c in FIG. 8. The branched cores are respectively bundled, covered by jackets and integrally arranged in matrix in each jacket providing the branched image fibers 11b and 11c. The branched image fiber 11b is connected to a light source of an analyzing apparatus and the branched image fiber 11c is connected to a spectrometer of the apparatus. The outer periphery of the image fiber 11 is covered by a light shading flexible coating 14 made of a non-transparent material. In this embodiment, a black polyvinyl chloride resin is used as the coating 14. A holder may be provided on the outermost periphery of the probe tip end 11a so as to protect the probe and to facilitate handling of the probe 10.

Assuming that the diameter of a core 13 is 30 μm and the jacket 12 has a thickness of 5 μm. in the sensing probe structured as described above, the distance l1 between the centers of the light illuminating core and the light receiving core, which is represented by a sum of the core diameter and twice the thickness of the jacket 12 between cores, can be made 40 μm or less, while the distance l in the conventional probe was about 100 μm. Therefore, the value of the depth d described with reference to FIG. 1, is now not more than one half of the conventional probe. Therefore, the sample area moves to the left of (b) in FIG. 3, namely, the area at which the optical density changes linearly, free from the influence of the scattering effect.

A condensing means such as the selfoc lens 4 may be provided at the end surface of the image fiber 11 also in this embodiment as shown in FIG. 8.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A fiber optic probe for measuring a reflectance spectrum, by emitting light onto a surface of a living body and by analyzing reflected light by spectrophotometry, comprising a fiber bundle having a first plurality of illuminating light transmitting optical fibers and a second plurality of light receiving optical fibers for receiving light transmitted by said first plurality of illuminating light transmitting optical fibers and reflected from said living body, said first and second plurality of optical fibers being arranged in parallel to and next to one another; cladding means enclosing all of said first and second optical fibers at least near a probe end of said fiber optic probe, and flat condenser lens means having a first flat surface in contact with end surfaces of said illuminating light transmitting optical fibers and with end surfaces of said light receiving optical fibers, said flat condenser lens means having, opposite said first flat surface, a second flat surface for contacting said living body surface, and wherein said cladding means comprise a heat shrinkable tube having a tube end projecting sufficiently in an axial direction for fixing said flat condenser lens means in a position for cooperation with said illuminating light transmitting optical fibers and with said light receiving optical fibers, said axially projecting tube end forming a radially inwardly constricted rim holding a periphery of said flat condenser lens means in place.

2. The fiber optic probe of claim 1, wherein said flat condenser lens means is detachably held by said constricted rim of said heat shrinkable tube forming cladding means.

3. A fiber optic probe for measuring a reflectance spectrum by emitting light onto a surface of a living body and by analyzing reflected light by spectrophotometry, comprising a cladding and a plurality of illuminating light transmitting optical fiber cores and a further plurality of light receiving optical fiber cores arranged next to each other in a matrix in said cladding, and condenser means (4) arranged with one flat surface in contact with end surfaces of all of said optical fiber cores, said flat condenser means having another flat surface for contacting said surface of said living body, and wherein said cladding comprises a heat shrinkable tube enclosing at least a probe end of said optical fiber cores and encircling a peripheral rim of said condenser means, thereby fixing said condenser means to said cladding and holding said condenser means to all of said fiber cores.

* * * * *

UNITED STATES PATENT AND TRADEMARK OFFICE
CERTIFICATE OF CORRECTION

PATENT NO. : 5,030,000
DATED : July 9, 1991
INVENTOR(S) : Masahiko Kanda

It is certified that error appears in the above-identified patent and that said Letters Patent is hereby corrected as shown below:

Column 4, line 48, delete "Each core 13 has a jacket 12";
          line 14, replace "having a jacket thickness of" by --All cores 13 in Fig. 7 are embedded in a common embedding material 12 and the thickness of the embedding material between neighboring cores 13 is--;
Column 5, line 12, replace "jacket 12" by --embedding material 12 between cores 13--;
Column 5, line 16, replace "a sum of" by --the sum of--, delete "twice", replace "jacket 12" by embedding material 12--;
          line 17, replace "cores" by --neighboring cores 13--, replace "40 μm or less" by --to be less than 40 μm--.

Signed and Sealed this

Twenty-fourth Day of November, 1992

Attest:

DOUGLAS B. COMER

*Attesting Officer*      *Acting Commissioner of Patents and Trademarks*

UNITED STATES PATENT AND TRADEMARK OFFICE
CERTIFICATE OF CORRECTION

PATENT NO. : 5,030,000
DATED : July 9, 1991
INVENTOR(S) : Masahiko Kanda It is certified that error appears in the above-identified patent and that said Letters Patent is hereby corrected as shown below:

Column 4, line 48, replace "Each core 13 has a jacket 12 having a jacket thickness of" by --All cores 13 in Fig. 7 are embedded in a common embedding material 12 and the thickness of the embedding material between neighboring cores 13 is--;

Column 5, line 6, replace "jacket 12" by --embedding material 12 between cores 13--;

line 9, replace "a sum" by --the sum--;

line 10, delete "twice";

line 11, replace "jacket 12" by --embedding material 12-- replace "cores" by --neighboring cores 13--; replace "40 μm or less" by --to be less than 40 μm--.

This certificate supersedes Certificate of Correction issued November 24, 1992.

Signed and Sealed this

Sixteenth Day of May, 1995

Attest:

BRUCE LEHMAN

*Attesting Officer*     *Commissioner of Patents and Trademarks*